United States Patent
Kehr et al.

(10) Patent No.: US 6,503,196 B1
(45) Date of Patent: Jan. 7, 2003

(54) ENDOSCOPE HAVING A COMPOSITE DISTAL CLOSURE ELEMENT

(75) Inventors: Ulrich Kehr, Ostfildern (DE); Jürgen Rudischhauser, Tuttlingen (DE); Klaus M. Irion, Liptingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/541,324

(22) Filed: Apr. 1, 2000

Related U.S. Application Data

(63) Continuation of application No. PCT/EP98/06207, filed on Sep. 30, 1998.

(30) Foreign Application Priority Data

Jan. 10, 1997 (DE) .......................................... 197 43 431

(51) Int. Cl.⁷ ................................................ A61B 1/06
(52) U.S. Cl. ........................ 600/176; 600/130; 600/177; 600/129
(58) Field of Search ................................ 600/176, 177, 600/169, 121, 129, 130, 133

(56) References Cited

U.S. PATENT DOCUMENTS

| | | | |
|---|---|---|---|
| 4,279,246 A | 7/1981 | Chikama ........................ 128/6 |
| 4,779,613 A | 10/1988 | Hashiguchi et al. ........... 128/6 |
| 4,942,867 A | 7/1990 | Takahashi et al. .............. 128/6 |
| 5,369,525 A | 11/1994 | Bala et al. ................... 359/435 |
| 5,377,669 A | * | 1/1995 | Schulz ........................ 385/117 |
| 5,402,768 A | 4/1995 | Adair ............................. 128/4 |
| 5,419,313 A | 5/1995 | Lemke ........................... 128/6 |
| 5,536,244 A | * | 7/1996 | Muller et al. ............. 228/124.1 |
| 5,554,099 A | 9/1996 | Heimberger et al. ......... 600/160 |
| 5,605,532 A | * | 2/1997 | Schermerhorn ............. 600/169 |
| 5,647,840 A | * | 7/1997 | D'Amelio et al. ........... 600/169 |
| 5,704,892 A | * | 1/1998 | Adair .......................... 600/121 |
| 5,718,663 A | * | 2/1998 | Wulfsberg ................... 600/160 |
| 5,944,656 A | * | 8/1999 | Pollack et al. .............. 600/176 |
| 6,110,105 A | * | 8/2000 | Durell ......................... 385/119 |
| 6,146,326 A | * | 11/2000 | Pollack et al. .............. 600/133 |

FOREIGN PATENT DOCUMENTS

| | | |
|---|---|---|
| DE | 3708124 A1 | 9/1987 |
| DE | 3923007 A1 | 1/1990 |
| DE | 3912720 C2 | 8/1992 |
| DE | 4211547 A1 | 10/1993 |
| DE | 4311577 A1 | 10/1994 |
| DE | 4341062 A1 | 6/1995 |
| DE | 19525995 C1 | 7/1996 |
| DE | 19743431 A1 | 4/1999 |

* cited by examiner

*Primary Examiner*—Linda C. M. Dvorak
*Assistant Examiner*—Jocelyn Ram
(74) *Attorney, Agent, or Firm*—St. Onge Steward Johnston & Reens LLC

(57) ABSTRACT

An endoscope has a head and an outer tube joined to it. Received in the outer tube is an inner tube in which optical components are received. Light guides are guided in the interstice between the interior space and outer tube. A closure element made of transparent material, which closes off the distal end of the outer tube in hermetically sealed fashion, is provided. The closure element has a window in the region of the inner tube. The window is surrounded by an opaque layer that shields the window radially from the entry of illumination light.

32 Claims, 5 Drawing Sheets

US 6,503,196 B1

ENDOSCOPE HAVING A COMPOSITE DISTAL CLOSURE ELEMENT

CROSSREFERENCE OF PENDING APPLICATION

This application is a continuation of pending international application PCT/EP98/06207 filed on Sep. 30, 1998.

BACKGROUND OF THE INVENTION

The present invention relates to an endoscope having a head at the proximal end; having an outer tube joined to the head; having an inner tube, received in the outer tube, in which optical components are received, a window made of transparent material being arranged at the distal end of the inner tube; and having light guides that are received in an interstice between inner tube and outer tube and are guided axially to the distal end of the interstice.

An endoscope of this kind is marketed by the Applicant. FIG. 12 of the appended drawings shows a longitudinal section through a distal end segment of an endoscope of this kind according to the existing art.

An inner tube R is received in outer tube A, which is permanently joined to the head of the endoscope. Inner tube R contains optical components, for example a lens arrangement, in particular a rod lens arrangement (called a "Hopkins optical system"), with which an image entering the inner tube at the distal end is guided to the proximal end of the endoscope. An eyepiece cup, against which an eye can be placed, is usually mounted at the proximal end of the endoscope.

In other configurations the optical components contain, for example, so-called optoelectronic charge-coupled device (CCD) sensors in the form of microchips, which convert the incoming image data into electrical signals that are sent in the proximal direction via electrical lines; after image processing, the image is displayed on a monitor.

The configuration of the head depends on the manner in which the image is viewed, i.e. either visually or by way of electronic image recording and playback, and the head can be simply a proximal end of a tubular element to which a camera module can be connected.

Since the optical elements in inner tube R constitute sensitive components, the distal end of the inner tube is closed off in hermetically sealed fashion by way of a window F. This closure is accomplished by the fact that a disk made of transparent material, usually a glass disk, is inserted into the open distal end of inner tube R and is joined sealedly and permanently to the inner side of the end segment of inner tube R, for example by soldering or adhesive bonding. In an interstice between the outer side of inner tube R and the inner side of the lager-diameter outer tube A, light guides in the form of glass fibers are guided from a proximal, usually laterally protruding, light connector to the outermost distal end of the endoscope, i.e. to the outermost distal end of the outer tube or inner tube, which end at the same level. The outermost distal ends of the glass fibers thus lie in the plane of the distally outer surface of disk F.

The individual glass fibers are cemented at the distal end to one another, and to the outer side of inner tube R and to the inner side of outer tube A.

The interior space of the endoscope is thus divided, in principle, into the interior space of inner tube R hermetically closed off toward the outside by window F, and the interstice between inner tube R and outer tube A in which light guides L are received, this space being closed off by the cemented join of the individual glass fibers to one another and the cemented join to the outer side of the inner tube and to the inner side of outer tube A.

This basic principle is also realized in those endoscopes whose interior space has not only these spaces (interior space of inner tube R, interstice) but also further spaces or ducts, for example for the passage of instruments or to form flushing or venting ducts. One such endoscope is known, for example, from U.S. Pat. No. 4,361,139. In addition to the inner tube, hermetically closed off by the distal-end window, in which the optical components are received, and an interstice in which the glass fibers are received, further ducts or spaces are also present. Here again, the light guides are guided to the distal end at the level of the outer plane of the window that seals the inner tube.

For reasons of sealing and stability, the inner tube is also joined to the head of the endoscope; the result of this is that the inner tube and the outer tube are joined at the proximal end via the head of the endoscope, and at the distal end via the cemented join.

Because of the widespread use of endoscopes in minimally invasive surgery, endoscopes of this kind are in frequent use and must be frequently cleaned or autoclaved. Such sterilization or autoclaving operations are performed in a temperature range from 130 to 140° C. In order to make endoscopes available again as quickly as possible after a procedure, so-called "flash" autoclaving techniques have been developed, in which the entire endoscope is heated to 143° C. and then quenched with cold water.

In view of the occurrence of pathogens that can withstand extremely high temperatures (one example being the so-called BSE pathogen), endoscopes must be exposed to extremely high temperatures.

It has now been found that the cemented points at the distal glass fiber end cannot withstand these severe stresses over the long term, and it is possible for leaks to occur which allow the penetration of contaminants or autoclaving media. The optical illumination system is disadvantageously influenced thereby, i.e. its illumination capability is weakened. The cemented points, which comprise a cured plastic material, can contain micropores which gradually can be penetrated by the media to which the distal end of the endoscope is exposed, so that bacterial pockets also exist.

The temperature fluctuations taking place during the autoclaving operations, in particular in flash autoclaving operations, cause considerable longitudinal mechanical stresses between the inner and the outer tubes which can result in breakage of the joins, in particular the joins between the cement and the outer side of the inner tube or the inner side of the outer tube in the region of the distal end, so that contaminants may then be able to penetrate over a large area and the endoscope thus becomes unusable.

DE 195 25 995 C1 discloses an endoscope whose distal end is closed off by a window. This window covers the entire end segment, i.e. both the region from which the light coming from the light guides emerges from the endoscope, and the distal end region of the inner tube in which the optical components are received. To prevent any coupling of light from the light guides into the optical system carrying the image, provision is made for at least one groove, extending parallel to the parting line between the cross-sectional regions of the image guide and the light guide and installed in one of the parallel surfaces of the window panel, to be provided as a light stop. The side surfaces or side flanks of the groove are intended either to reflect back or otherwise to prevent the crossover of light rays reflected transversely through from the light guide to the image guide.

Cross-reflection can thereby be considerably decreased but not eliminated, since the groove depth, weighed against the remaining mechanical strength of the window panel, determines the degree to which reflection is suppressed.

It is disadvantageous in this context that light spillover from the illumination system into the image-carrying system in the transverse direction cannot be completely eliminated, and that the grooves cause weakening of the mechanical stability of the one-piece window panel. This window panel cannot withstand the severe mechanical stresses occurring, for example, during handling, in particular during cleaning and sterilization, or those resulting from a fall.

DE 42 11 542 C2 discloses a protective cover for the distal end of the endoscopes that has a first component which has a mount that can be placed onto the end of the inner tube which receives the optical components. The mount itself carries centeredly a window with an optical effect, through which light can enter the optical system from the outside.

At the distal end the window projects beyond the mount, and a second part which covers the remaining end surface of the distal end of the endoscope is slid over the projecting region, this part being joined to the outer end of the outer tube.

In order to prevent illumination light from spilling over in the transverse direction, an opaque layer is provided at least on the contact surfaces between the outer side of the window projecting from the mount and the inner side of the second part.

In order to ensure a hermetically sealing closure, provision must be made for a seal between the distal end of the inner tube and the mount, also for a hermetically sealing closure between the mount and the window inserted into the mount, and additionally for a hermetically sealing closure between the outer covering part and the window received therein, and between the outer part and the annular frontal end of the outer tube. Several different materials encounter one another in this critical sealing region, i.e. on the one hand the sapphire protective cover and the material of the mount, and the materials of the inner tube and outer tube. Since different materials also have different coefficients of expansion, it is inherent in the system that with this design, leaks can occur in long-term service. In addition, the protective cover is made up of numerous parts that must be exactly matched to one another, and these must be sealingly joined both to the inner tube and to the outer tube. The mount, which also must be opaque—because otherwise light could enter the optical system in the transverse direction from the light guides via the mount, since the mount rests directly against the light guides—covers a considerable cross section of the distal end of the endoscope, so that this cross section is not available either for light output from the light guides or for light entry into the image guide.

If one imagines this design in the context of the endoscope illustrated in FIG. 12 of the present Application, it is evident that a mount surrounding the window would need to occupy a considerable portion of the space occupied around the window by the light guides. This means that the light output surface would be considerably reduced, and the space behind would be regarded, in terms of illumination engineering, as "dead space."

It is therefore the object of the present invention to provide a remedy, and to describe a closure of the distal end of the inner tube, and of the interstice in which the light guides are received, that is permanently sealed and that is simple to bring about.

SUMMARY OF THE INVENTION

According to the present invention, the object is achieved in that a closure element made of transparent material is provided, which closes off the distal end of the outer tube in hermetically sealed fashion at least in the region of the inner tube and of the interstice receiving the light guides; that the closure element has in the region of the distal end of the inner tube the window through which light can enter the inner tube; and that the window is surrounded circumferentially by an opaque layer which shields the window radially from the entry of illumination light that, coming from the light guides, is guided through the closure element and emerges at the distal end.

Provision is now made according to the present invention, in contrast to the existing art mentioned initially, for closing off in hermetically sealed fashion not the inner tube which carries the optical components, but rather the outer tube, both in the cross-sectional region of the inner tube and in the cross-sectional region of the interstice receiving the light guides. The distal closure of the interstice in which the light guides are received is no longer brought about by a cemented point, but rather by a separate closure element. In other words, the light guides extend not to the outer side but only as far as the inner side of the closure element, and are covered by it on the outside. Because the entire closure element is configured from transparent material, the illumination light emerging from the light guides at the distal end can emerge through the closure element to the exterior, and because of the window in the closure element it is possible to allow the image to pass from the outer side into the inner side of the inner tube.

The opaque layer which surrounds the window circumferentially ensures that no illumination light passing through the closure element can enter from it, as stray light, into the interior space of the inner tube. The opaque layer essentially prolongs the inner tube, and shields it radially from the illumination light. The material of the opaque layer can be selected as desired, with the stipulation that a sealed closure between the window and this surrounding element must be possible.

Because the closure element is joined in hermetically sealed fashion to the outer tube, it is no longer necessary for the distal end of the inner tube also to be joined permanently to the closure element, since the region in which the inner tube terminates at the distal end, and the region in which the light guide fibers terminate, is hermetically closed off by the closure element. This therefore eliminates the need for an additional mechanically permanent join between the distal end of the inner tube and the outer tube, in addition to a further join at the proximal end. It is possible to join the inner tube mechanically to the outer tube at only one point, as a result of which thermal length differences between the inner and outer tubes can no longer cause any mechanical length stresses.

This configuration makes it possible for the interior spaces of the inner tube and the interstice in which the light guides are received to be closed off permanently, in hermetically sealed fashion, toward the outside, so that leaks cannot occur either because of the manner or sealing or joining at the distal end, or because of length differences between the inner tube and outer tube.

If all that is present in the endoscope shaft is the inner tube with the optical components and the interstice in which the light guides pass to the distal end, the closure element thus closes off at the distal end the entire inside cross section of the outer tube which represents the endoscope shaft. If further ducts or passages for the passage of instruments or liquids or gases are present in the shaft, the closure element closes off the region that corresponds to the inner tube and to the distal opening of the interstice at which the light guides terminate distally. The sealed closure by way of the simply constructed and simply configured closure element can be brought about easily and reliably by adhesive bonding or soldering. The closure element supports and holds the window, so that no additional mount is necessary. A join between the window and inner tube is also eliminated.

In a further embodiment of the invention, the closure element is made up of the window, an opaque layer covering its circumferential enveloping surface, and an element surrounding it.

The advantage of this feature is that the closure element is configured as a composite element, so that it can be adapted to the respective cross-sectional geometries of the inner tube and of the interstice in which the light guides are received; and the opaque layer can also accordingly be adapted in each case to the geometry of the inner tube in order to shield the inner tube from any radial spillover of emerging illumination light. The hermetically sealed join between the closure element and outer tube, and the hermetically sealed join between the window and the element surrounding it, can be accomplished by way of actions known per se, for example soldering, as has been done with the hermetically sealed join between the window and the inner tube in the case of the existing art cited initially.

The element surrounding the centered window can vary depending on the geometry and arrangement of the inner tube relative to the outer tube. With a coaxial arrangement of outer tube and inner tube, it is configured as a ring; with a non-coaxial arrangement it is configured as a sickle-like structure that in all cases transparently covers the corresponding space that is not covered by the window, so as to allow illumination light to emerge. If the inner tube is placed, for example, along a surface line on the inner side of the outer tube, the element has in cross section a shape that is not completely continuous, i.e. in this case the inner tube is not completely surrounded by light guides.

In a further embodiment of the invention, the opaque layer is configured in such a way that it provides not only shielding but also a hermetically sealed join between the window and the element surrounding it.

The advantage of this feature is that the opaque layer performs two functions, i.e. serves not only as a shield but also as a joining material between the window and the element surrounding it.

In a further embodiment of the invention, the opaque layer is made of a material which has a coefficient of thermal expansion that lies in the range of the coefficients of thermal expansion of the materials of the window and of the element surrounding it.

The considerable advantage of this feature is that the join can withstand the severe thermal stresses even over the long term.

In a further embodiment of the invention, the opaque layer is applied on the circumferential enveloping surface of the disk and/or on the radially inner enveloping surface of the annular element.

This feature offers the possibility of applying the layer of opaque material as a function of the point at which it is most favorable. If the window is configured as a round disk that is cut from a rod-shaped material, for example, it may be advantageous to equip its circumferential outer side with the opaque layer, or to coat the rod-shaped material from which it is cut, which can easily be done, for example, by immersing a rod in a corresponding medium.

In some circumstances it may be even more favorable if the radially inner enveloping surface of the element surrounding the disk is coated with the opaque layer.

Especially when the material of the opaque layer is also intended simultaneously to ensure the sealed permanent join between these two components, it may be advantageous to coat both enveloping surfaces.

In a further embodiment of the invention, the opaque layer is made of a metallic material that is applied onto the enveloping surfaces as a prefabricated coating layer or by sintering or by vacuum deposition.

These features have the considerable advantage that the opaque layer can be easily and reliably applied depending on the design that is present.

In one easily implemented case, the opaque layer is configured as a metal tubular segment that is slid on so as to fit on the outer enveloping surface of the window. If the metallic material also has the properties of a solder material, it can simultaneously be utilized to join the two transparent components of the closure element, specifically by the fact that these two are soldered to one another.

Vacuum deposition or the sintering on of powdered material will be advantageous if complexly shaped enveloping surfaces need to be coated. In this context, vacuum deposition can be accomplished by a chemical (CVD) or physical (PVD) vapor deposition method.

In a further embodiment of the invention, the radially outer enveloping surface of the element surrounding the window is also coated with a material that creates a hermetically sealed join with the inner side of the distal end of the outer tube.

The advantage of this feature is that if applicable, the composite element made up of the window and the element surrounding it is produced first, and the outer circumferential layer is subsequently or simultaneously applied onto the enveloping surface of the element, so that this composite element then simply needs to be inserted into the distal end of the outer tube and joined to it in accordance with the configuration of the layer, for example soldered.

In a further embodiment of the invention, the outer enveloping surface of the element is coated with the same material that provides the join between the element and window.

The advantage of this feature is that the sealed join between the window and the element surrounding it on the one hand, and between this composite element and the inner side of the outer tube on the other hand, can be accomplished in one operation.

In a further embodiment of the invention, the opaque layer is configured between the window and the element surrounding it, on the element side, as a light-reflecting layer.

The considerable advantage of this feature is that illumination light is not absorbed by the enveloping surface of the window, but rather is reflected, and the illumination remains available.

In a further embodiment of the invention, the radially outer enveloping surface of the element is equipped with a light-reflecting layer.

This feature has the same advantageous effect as the embodiment mentioned previously; in this embodiment, illumination light encountering the enveloping surface from this side is now also reflected and the illumination is made available.

This is advantageous in particular if the two enveloping surfaces do not run parallel to one another but rather, for example in the case of endoscopes having angled viewing directions, may run at an angle to one another.

In a further embodiment of the invention, the opaque layer, and/or the material for joining the components of the closure element to one another and/or to the outer tube, and/or the light-reflecting layer, are made of a solderable material.

The advantage of this feature is that with a solderable material it is possible, by way of a heat treatment and delivery of solder, to create the opaque layer, the join among the individual components, and—if a suitable metallic solderable material is present—also simultaneously the light-reflecting layer. This feature thus promotes simple manufacture of the sealing join among the individual components of the closure element, and the join between the closure element and outer tube.

In a further embodiment of the invention, the element is configured as a ring in which the window sits in centeredly fitted fashion.

The advantage of this feature is that both the ring and the window have simple geometries, in each case with cylindrical enveloping surfaces that can easily be coated with the corresponding materials, be they an opaque layer or materials for joining them to one another or for joining to the outer tube.

In a further embodiment of the invention, when the viewing directions are angled, the closure element is arranged obliquely with respect to the longitudinal axis of the outer tube.

The advantage of this feature is that the closure element according to the present invention can also be used with endoscopes that allow angled viewing directions.

In a further embodiment, the outer tube is configured as a tubular element which can be pulled off from the endoscope and is slidable over a shaft tube which bears the inner tube; and the closure element closes off the pull-off tubular element at the distal end in hermetically sealed fashion.

The considerable advantage of this feature is that the outer tube, which is closed off in hermetically sealed fashion by way of the closure element, can be pulled off after the endoscope has been used.

Since only the outer side and the distal end region of the outer tube can come into contact with contaminants during an endoscopic procedure, these contaminants are present on the outer side of the outer tube and on the closure element. Since these components are now configured as a tubular pull-off element, only these components need to be sterilized, whereas the remaining components, i.e. the endoscope head along with the shaft tube, need at most to be cleaned.

It is now possible, as a result, to incorporate into the inner tube components that are sensitive to high temperature, for example appropriate chips, which are then not exposed to high temperatures during autoclaving operations, especially during flash autoclaving.

This considerably simplifies the handling, in particular, of endoscopes on which video cameras are mounted; this is because it is not necessary to disassemble the entire endoscope, but instead all that is needed is to pull off the outer tube together with the closure element that hermetically closes it off at the distal end, in order to subject it to cleaning and autoclaving operations.

In a further embodiment of the invention, the tubular element is configured as a rigid tube.

The advantage of this feature is that the pull-off outer tube is configured as a rigid stable element, and thus can be correspondingly handled for cleaning and stabilization purposes.

In a further embodiment of the invention, the tubular element is configured as a flexurally limp hose.

The advantage of this feature is that the pull-off outer tube can be slid onto and removed from the endoscope as a kind of sheath, and can be configured, for example, as a disposable element so that cleaning and sterilization operations can be eliminated.

In a further embodiment of the invention, the light guides are installed in the pull-off tubular element.

The advantage of this feature is that it creates a subassembly which can be slid as a compact unit onto an endoscope that contains only the optical components.

In a further embodiment of the invention, there are provided on the closure element supports against which the distal end of the shaft tube comes into contact in a defined position.

The advantage of this feature is that with the embodiment having the pull-off tubular element, the outer tube arrives in an accurately defined position relative to the shaft tube in whose inner tube the optical system is received. This means that the window of the closure element comes to rest in front of the inner tube of the shaft tube in an exactly defined position, so that the image is not influenced. In this case the inner tube is then closed off by a closure disk.

In a further embodiment of the invention, a light connector in the proximal region of the endoscope, to which the proximal end of the light guides is guided, is also closed off in hermetically sealed fashion by a light connector window.

The advantage of this feature is that the space in which the light guides are received, which is critical in terms of the penetration of contaminants, is now closed off in hermetically sealed fashion at both ends, i.e. at both the proximal and the distal end.

In a further embodiment, the light connector window of the light connector is mounted in hermetically sealing fashion in the same way as the closure element.

The advantage of this feature is that both sealed joins, i.e. both that of the distal-end closure element and that of the proximal closure of the light connector, can be effected simultaneously, for example by way of a heat-treatment operation to solder the windows to the corresponding components.

In a further embodiment of the invention, the closure element is configured, in the region through which the illumination light is passed, as an optically effective element, in particular as a diffuser or a focusing lens.

The advantage of this feature is that the closure element functions in the illumination light passthrough region not only as a light opening but as an optically active element which imparts certain properties to the illumination light.

In a further embodiment of the invention the closure element is shaped, in the region through which the illumination light is passed, in such a way that a deflection of the illumination light out of the light axis is accomplished.

This feature has the advantage that merely by way of the conformation, certain directional properties are already imparted to the illumination light; these can, of course, also be additionally combined with the aforementioned feature.

In a further embodiment of the invention, the shaping is such that flattened areas are present on the outer side and/or on the inner side of the closure element.

The advantage of this feature is that such flattened areas are very easy to implement, and that a desired directional component is imposed on the illumination light by the geometry of the flattened areas or the orientation angle of the flattened areas relative to the light guide axis.

In a further embodiment of the invention, the window is configured as an optically effective element, in particular as a lens and/or as a filter.

The advantage of this feature is that the window not only serves to admit the image, but also already represents an element of the optical components, so that in overall terms the total number of optical components can be reduced.

In a further embodiment of the invention, the closure element is configured so as to absorb IR light.

The considerable advantage of this feature is that the closure element is heated as a result of this absorption of IR light, i.e. of heat radiation.

In endoscopes, there exists the danger that upon insertion into a body—whose temperature is usually higher than the ambient temperature at which the endoscope was previously—the distal closure element may fog up. This can be prevented by the fact that due to the absorption of heat from the light passing through the closure element, it is heated to a temperature such that fogging cannot occur. The closure element according to the present invention thus additionally functions as an "anti-fogging" unit.

As previously mentioned, a relatively large space around the centered window is available as a passthrough surface for the illumination light. If the illumination light has a specific spectral composition, it is now possible for the illumination light to contain a proportion of IR light suitable for the particular application, which is absorbed by the closure element and is utilized, by thermal conduction, to heat the closure window (i.e. the closure element) over its entire cross section. Local overheating or the like can thereby also be prevented.

In a further embodiment of the invention, the opaque layer which surrounds the window is transparent to IR light.

The advantage of this feature is that the inherently opaque layer enhances the transfer of IR radiation toward the window from the region of the closure element through which the illumination light passes, and thus ensures controlled and rapid heating of this region which is particularly affected by moisture fogging.

In a further embodiment of the invention, the inner side of the window and/or the outer side of the closure element is coated with a layer that reflects IR light.

The considerable advantage of this feature is that IR light coupled into the closure element cannot emerge from it again, but rather is repeatedly reflected by the IR-reflecting layers in the window and ensures that it heats up in rapid and controlled fashion. In particular, IR light components of the illumination light are reflected at the outlet side of the region surrounding the window, and are thus trapped in the closure element.

The closure window operates as a kind of IR light trap, which removes IR light from the illumination light, delivers it in controlled fashion to the centered window which closes off the image-carrying system, and there ensures heating by reflection.

In a further embodiment of the invention, the inner side of the closure element is coated, in the region in which the light guides terminate, with a semi-permeable layer that is transparent in the illumination direction and blocks light in the opposite direction.

This feature enhances the aforementioned function of the closure element as an "IR trap."

All in all, therefore, the closure element is configured in such a way that the illumination light can pass through in the illumination direction, the IR light is absorbed and is utilized for heating, and any emergence of absorbed IR light is prevented over all the outer surfaces, i.e. emergence is prevented over the entire inner side and over the entire outer side of the closure element due to the reflective configuration of the outer surfaces.

A particular embodiment of the invention proposes a method for manufacturing a closure element for closing off the distal end of an endoscope that is characterized by a) preparing a long, rod-shaped, transparent material having the cross section of the window;

b) preparing a long, tubular, transparent material into whose inner cavity the long rod-shaped material can be introduced so as to fit approximately;

c) providing an opaque layer between the outer side of the rod-shaped material and the inner side of the cavity;

d) sliding the rod-shaped material and tubular material into one another;

e) joining the outer side of the rod-shaped material in permanent and sealed fashion to the inner side of the cavity; and f) cutting the assemblage of rod-shaped material and tubular material into individual disk-shaped closure elements.

The advantage of this feature is that the individual closure elements can be manufactured in simple fashion, which contributes to achieving the object in terms of easy implementation of the closure. Rod-shaped and tubular transparent materials can be manufactured easily, dimensionally accurately, and in correspondingly long lengths on an industrial scale, so that a very large number of closure elements can be obtained from one single assemblage.

Once the assemblage has been created, a check can be made as to whether the join is both sealed and opaque, and the operation of cutting the individual closure elements can be performed.

In a particular embodiment of the invention, in step c) the outer side of the rod-shaped material is equipped with the opaque layer.

The advantage of this feature is that it can be performed very easily, for example by immersing the rod into a corresponding solution and then applying the corresponding material, uniformly and at a predetermined thickness, onto the outer side of the rod-shaped material. A corresponding inspection can be made even at this early point in time.

After joining, whether by way of an adhesive bonding operation or a sintering operation, the join can readily be checked visually or optically, which also contributes to simplicity of manufacture.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be explained and described in more detail below with reference to several selected exemplary embodiments in combination with the appended drawings, in which.

DETAILED DESCRIPTION OF PREFERRED EMBODIMENTS

Figure 1:
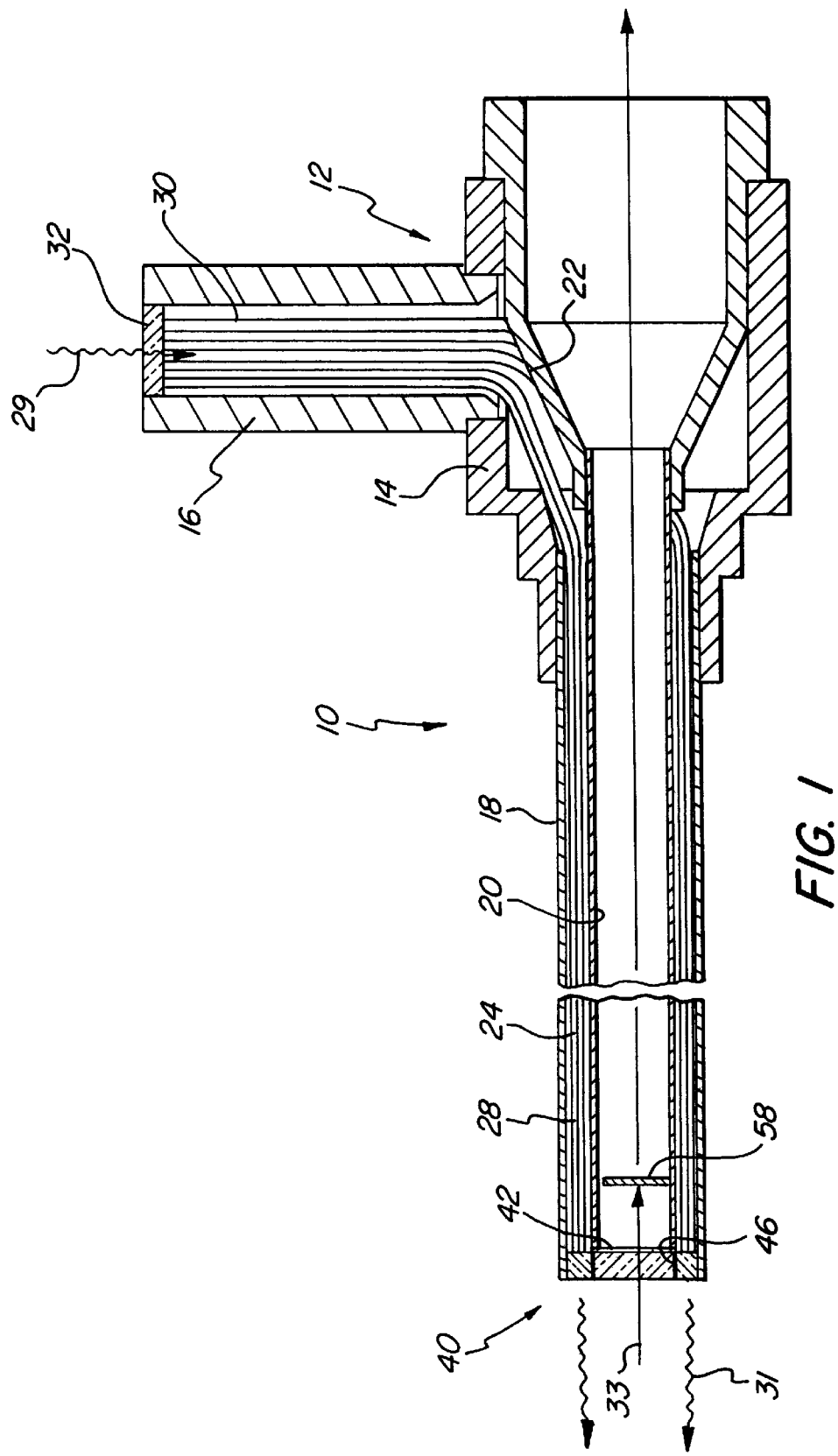
FIG. 1 shows, in highly schematic fashion, a longitudinal section of an endoscope having a closure element according to the present invention.
Figure 3:
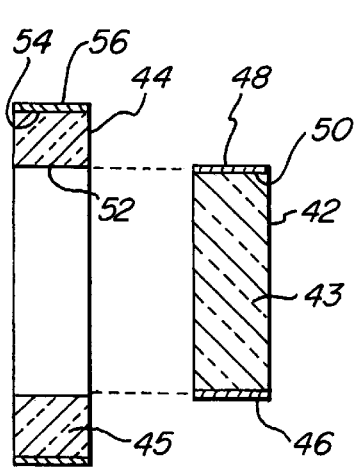
FIG. 3 shows a representation, comparable to the sectioned representation of FIG. 2, of the components of the closure element in an exploded representation.
Figure 2:
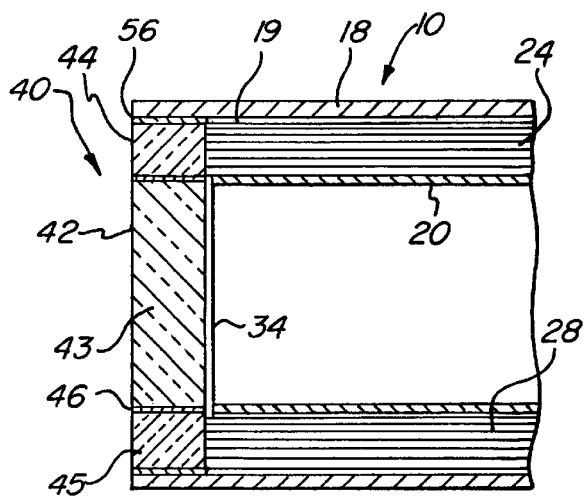
FIG. 2 shows a greatly enlarged longitudinal section of the endoscope of FIG. 1 in the region of its distal end.

An endoscope 10 shown in FIGS. 1 through 3 has proximally a head 12.

Head 12 has a housing 14 from which a light connector 16, in the form of a tubular fitting, projects laterally.

Housing 14 is joined, permanently and sealedly with respect to the outside, to a shaft-like outer tube 18, for which purpose the latter is slid into housing 14 and soldered to it.

Received in outer tube 18, coaxially therewith, is a smaller-diameter inner tube 20 that is permanently joined to an eye-piece extension 22 which is received in the interior space of housing 14. At the proximal end, eyepiece extension 22 is sealedly joined to an eyepiece or to an eyepiece cup placed thereon when inner tube 20 serves to receive an optical lens system (not shown here in further detail).

Because the outside diameter of inner tube 20 is smaller than the inside diameter of outer tube 18, an interstice 24 is created between them.

The purpose of interstice 24 is to receive light guides 28 in the form of a bundle of glass fibers 30 that are guided from the outer end of light connector 16 to the outer proximal end of inner tube 20, as is visible in particular in the sectioned representation of FIG. 2. A light connector window 32 closes off light connector 16 hermetically and sealedly at the proximal end, but allows light proceeding from a light source to enter the glass fibers, as is indicated in FIG. 1 by an arrow 29.

Outer tube 18 is closed off in hermetically sealed fashion at the distal end by a closure element 40.

For that purpose, outer tube 18 projects distally beyond inner tube 20, specifically by an amount equal to the axial thickness of closure element 40.

Closure element 40 comprises a window 42 made of glass, which in the exemplary embodiment shown takes the form of a flat, round disk 43.

Element 44 surrounding disk 43 is configured as a ring 45 that is also manufactured from glass.

The outside diameter of disk 43 corresponds approximately to the inside diameter of inner tube 20.

The outside diameter of ring 45 corresponds approximately to the inside diameter of outer tube 18.

The outer enveloping surface 50 of disk 43 is equipped with an opaque layer 46. Opaque layer 46 comprises a tubular segment 48 of a metallic material having solder properties, which is fused to disk 43. The outer enveloping surface 54 of ring 45 is similarly equipped with a metallic layer 56.

It is apparent from the representation of FIG. 3 that disk 43, together with its opaque layer 46 applied onto it, can be inserted so as to fit into ring 45.

The assemblage of disk 43 and ring 45 together with the outer circumferential layer 56 can just be slid into the segment in outer tube 18 projecting beyond inner tube 20. After a heat treatment, enveloping surface 50 of disk 43 is joined in hermetically sealed fashion to ring 45, and the latter in turn in hermetically sealed fashion to the inner side of outer tube 18, so that a hermetically sealed closure is thereby accomplished.

As is apparent in particular from FIG. 2, opaque layer 46 represents a kind of prolongation of inner tube 20, and thus shields the interior space of inner tube 20 from the radial entry of illumination light that emerges through ring 45, as indicated in FIG. 1 by arrows 31. The image can enter, through disk 43, into the interior space of inner tube 20, as indicated in FIG. 1 by an arrow 33, and is then guided via corresponding optical components (only one component 58 being schematically indicated) to the proximal end of head 12.

As is evident from the representation of FIG. 2, distal end 34 of inner tube 20 is not permanently joined either to closure element 40 or to outer tube 18, so that no stresses can occur in this region due to differences in longitudinal expansion in response to temperature fluctuations. For purposes of illustration, the width of the gap as shown in FIG. 2 has been kept large.

Since the distal end of interstice 24 at, which glass fibers 30 end, is hermetically sealed toward the outside, the join or positional retention of glass fibers 30 does not need to meet stringent sealing requirements, as is the case with the existing art cited initially.

FIG. 3 shows the manner in which closure element 40 can additionally be configured as an "anti-fogging" unit. Both the inner and the outer side of window 42 are coated with a layer 47 of material that reflects IR light. The outer side of ring 45 is also coated with such a layer 47.

Opaque layer 46 is configured in such a way that it is transparent to IR light but blocks visible light.

In addition, the inner side of ring 45 is coated with a semitransparent layer 49. This layer 49 allows all the illumination light of light guides 28 to pass in the illumination direction, but blocks it in the opposite direction.

When the assemblage of ring 45 and disk 43 is then inserted into endoscope 10 as shown in FIG. 2 (the additional layers are not shown here for the sake of simplicity), it is thus evident that closure element 40 serves as an IR trap. The illumination light delivered by light guides 28 passes through closure element 40 in the region of ring 45. IR light components of the illumination light are reflected by layer 47 and result in heating of ring 45. Semitransparent layer 49 reflects this reflected light again. Because opaque layer 46 is transparent to IR light, reflection and thus absorption of IR light also takes place in disk 43. Since disk 43 is coated on both sides with layer 47 which reflects IR light, the IR light coupled in by way of the illumination light is repeatedly reflected and results in rapid and homogeneous heating of the assemblage of disk 43 and ring 45, i.e. of the entire closure element 40, thus preventing any fogging of the outer side.

Closure element 40 can be manufactured by first preparing a long, rod-shaped, transparent glass material having the cross section of disk 43, whose outer side is coated with opaque layer 46. This rod is then inserted into a tube which corresponds to the contour of ring 45. This assemblage is then correspondingly treated, to create the sealed and permanent join between the outer side of disk 43 and the inner side of ring 45, depending on how opaque layer 46 is configured, i.e. as an adhesive join or as a soldered or sintered join. This assemblage is then cut into disk-shaped closure elements 40, and the corresponding coatings can then be applied if the configuration of the closure element as an IR trap or "anti-fogging" unit is desired.

Figure 4:
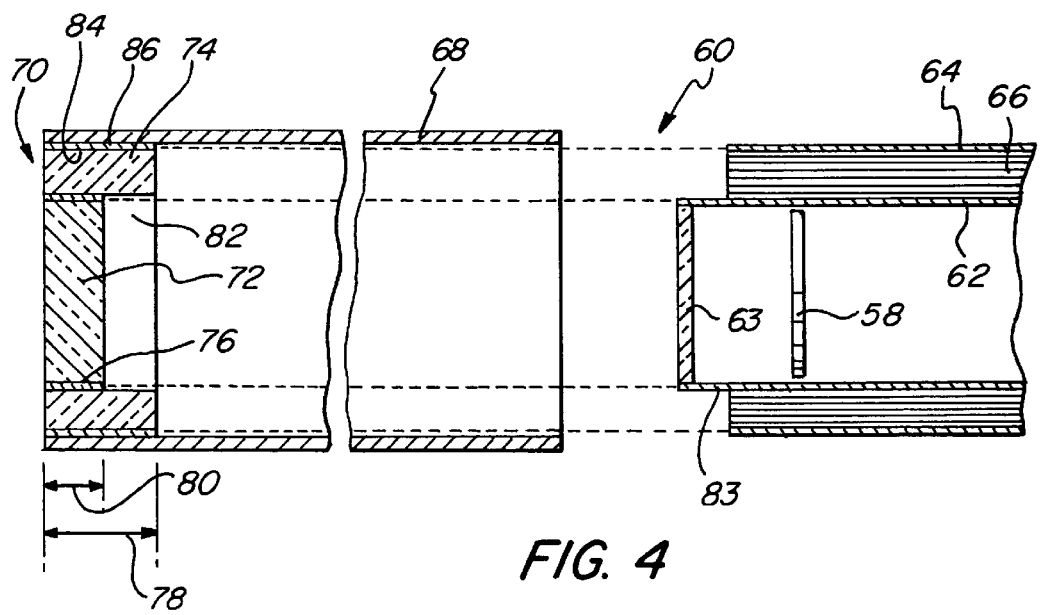
FIG. 4 shows a longitudinal section of a distal end region of a further exemplary embodiment of an endoscope according to the present invention having a pull-off outer tube, the end of which is closed off in hermetically sealed fashion by a closure element according to the present invention.

FIG. 4 shows a further exemplary embodiment of an endoscope 60. Endoscope 60 has an inner tube 62 that is closed off sealedly at the distal end by a closure window 63. Inner tube 62 is surrounded by an outer shaft tube 64; light guides 66 are received in the interstice between outer shaft tube 64 and inner tube 62.

As is evident from FIG. 4, inner tube 62 projects a certain amount beyond the distal end of light guides 66.

A tubular element 68, whose length corresponds to the overall length of the shaft of endoscope 60 and which can be pulled off from outer shaft tube 64, can be slid over said tube 64.

Tubular element 68, which is open at the proximal end, is closed off toward the outside at the distal end in hermetically sealed fashion by way of a closure element 70.

As described previously, closure element 70 has a window 72 in the form of a disk that is received in an annular element 74. As also described previously, window 72 is surrounded by an opaque layer 76.

The axial length 78 of annular element 74 is greater than the axial length 80 of window 72, specifically by an amount equal to that by which inner tube 62 protrudes beyond light guides 66.

The result is to create a support 82 into which projection 83 can come to rest in defined fashion.

Since closure element 70 is joined in hermetically sealed fashion to tubular element 68 by way of the outer circumferential layer 86 on the outer enveloping surface of annular element 74, and window 72 is joined (also in hermetically sealed fashion) to annular element 74 by way of opaque layer 76, the result is a hermetically sealed distal closure of the pull-off tubular element 68. When element 68 has been slid completely onto outer shaft tube 64, window 72 comes to rest directly against closure window 63 of inner tube 62. Opaque layer 76 then once again constitutes a prolongation of inner tube 62, and thus once again assumes the shielding function with respect to the illumination light emerging through annular element 74. Once a procedure has been performed with endoscope 60, pull-off element 68, together with closure element 70, can be pulled off and cleaned or sterilized. Since element 68 covers the entire shaft of endoscope 60, the head of endoscope 60 and its outer shaft tube 64 are not soiled or contaminated by bacteria, so that a simple cleaning is sufficient. It is thus possible to incorporate into inner tube 62, for example, a temperature-sensitive optical element 58' in the form of a CCD sensor, since this component of endoscope 60 does not need to be subjected to the high temperatures of autoclaving.

In the exemplary embodiment shown, element 68 is configured as a metal tube. It can also be made of a flexurally limp plastic material that can be applied onto shaft tube 64 as a sheath and can be discarded after removal.

Figure 5:
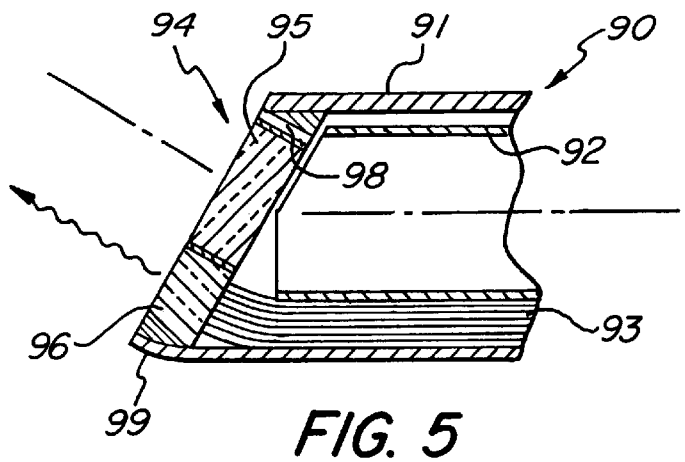
FIG. 5 shows a longitudinal section, comparable to the representation of FIG. 2, of a further exemplary embodiment of an endoscope having an angled viewing direction.

FIG. 5 shows a distal end region of an endoscope 90 that allows an angled viewing direction.

An inner tube 92 is received in outer tube 91, light guides 93 being arranged in the interstice.

A closure element 94 closes off the distal end of outer tube 91 in hermetically sealed fashion, as has also been described previously, i.e. closure element 94 has a disk 95 and a ring 96 surrounding the latter. An opaque layer 98 provides shielding against the illumination light.

A curved end 99 of outer tube 91 fits around the outer enveloping surface of closure element 94.

In a further exemplary embodiment of an endoscope 100 shown in FIG. 6, once again an angled viewing direction is possible; outer tube 101, which receives an inner tube 102 and corresponding light guides 103, is closed off in hermetically sealed fashion by way of a closure element 104 that comprises a centered disk 105 which is surrounded by a ring 106.

An opaque layer 108 provides shielding of the illumination light.

A flanged rim 109 of outer tube 101 fits around closure element 104.

Figure 6:
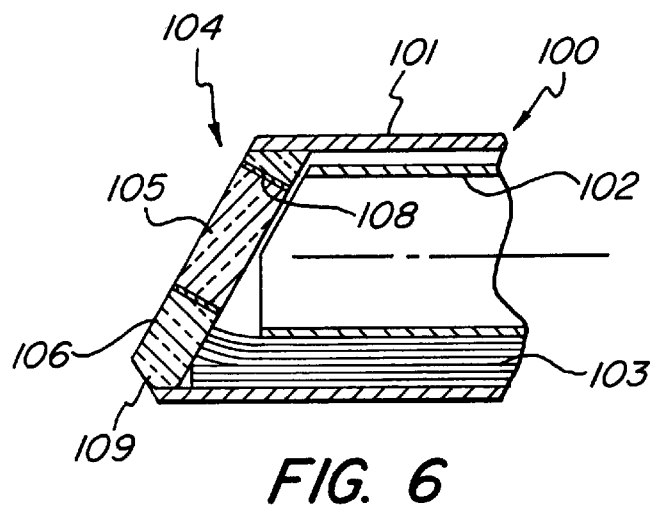
FIG. 6 shows a section, comparable to the representation of FIG. 5, of a further exemplary embodiment of an endoscope having an angled viewing direction.

In the exemplary embodiments shown in FIGS. 5 and 6, opaque layers 98 and 108 are oriented in terms of their axial extension in the direction of the angled portion.

Figure 7:
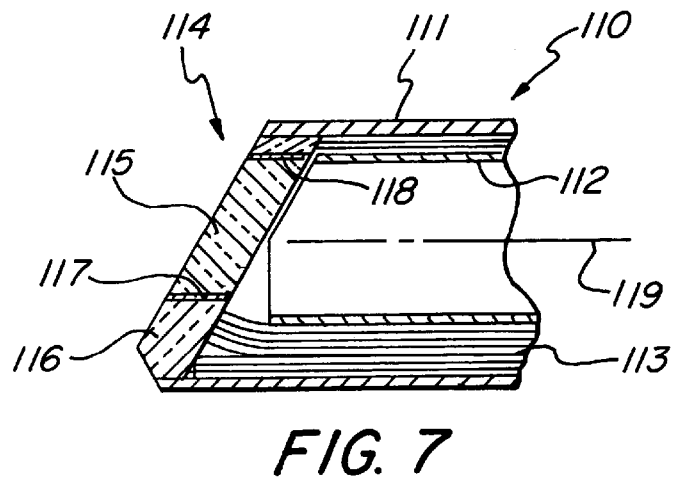
FIG. 7 shows a representation, comparable to the sectioned representations of FIGS. 5 and 6, of a further exemplary embodiment of an endoscope having an angled viewing direction.

In the exemplary embodiment of an endoscope 110 shown in FIG. 7, a closure element 114 constituted by a disk 115 and a ring 116 is provided in an outer tube 111 that receives an inner tube 112 and light guides 113. Although this endoscope 110 allows an angled viewing direction, an enveloping surface 117 of opaque layer 118 is oriented in the direction of longitudinal axis 119 of outer tube 111. This makes possible particularly good shielding with respect to the illumination light.

Figure 8:
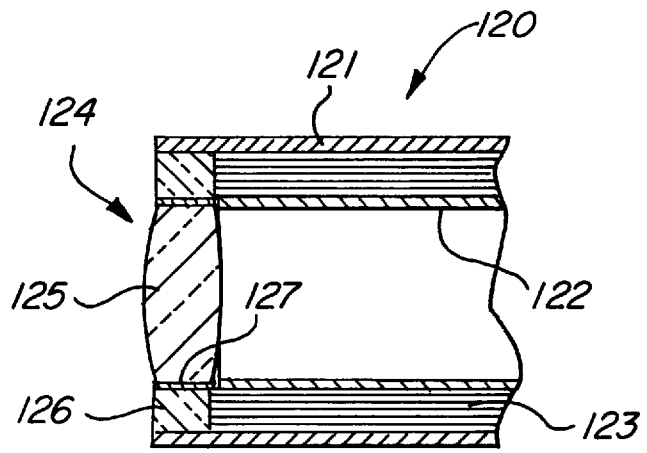
FIG. 8 shows a representation, comparable to the sectioned representation of FIG. 2, of a further exemplary embodiment having an optically effective window.

In the exemplary embodiment of an endoscope 120 shown in FIG. 8, a closure element 124 whose window 125 is configured as a lens is provided in an outer tube 121 that receives an inner tube 122 and light guides 123. Window 125 is surrounded by a ring 126, and opaque layer 127 once again lies between them. Window 125 is thus already part of the optical system in inner tube 122.

Figure 9:
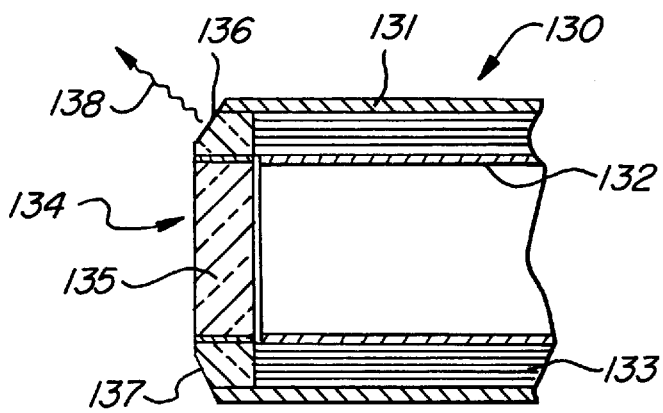
FIG. 9 shows a section, comparable to the sectioned representation of FIG. 8, through a further exemplary embodiment having flattened areas in the region of the closure element in which the illumination light emerges.

In the exemplary embodiment of an endoscope 130 shown in FIG. 9, a closure element 134 whose window 135 is configured as a planar flat disk is provided in an outer tube 131 that receives an inner tube 132 and light guides 133. Ring 136 surrounding window 135 has a flattened area 137 on the outer side. It is possible by way of flattened area 137 to laterally deflect the light coming from light guides 133, as indicated by an arrow 138.

Figure 10:
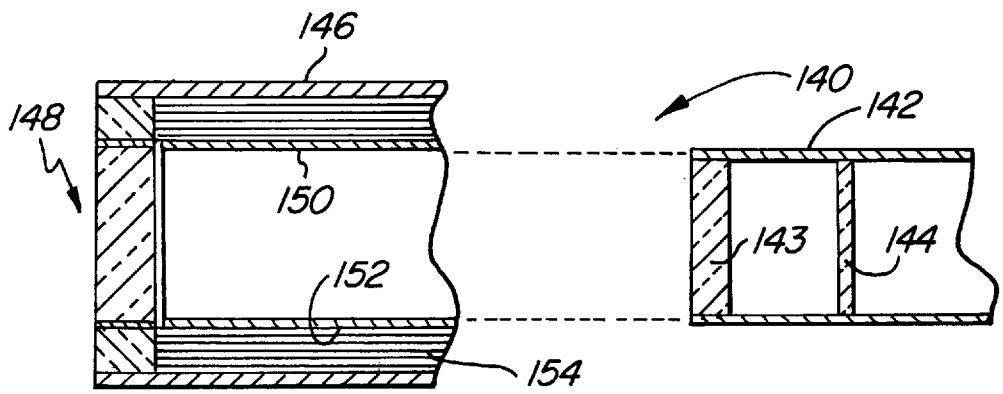
FIG. 10 shows a representation, comparable to the representation of FIG. 4, of an exemplary embodiment having a pull-off outer tube in which the light guides are received.

In the exemplary embodiment of an endoscope 140 shown in FIG. 10, the principle implemented is the same as that already described in conjunction with FIG. 4.

An inner tube 142, which is closed off distally in hermetically sealed fashion by a closure window 143, serves to receive optical components 144. An outer tube in the form of a tubular element 146 is closed off at the distal end with a closure element 148, as described in conjunction with FIGS. 1 through 3.

A further inner tube 150 is inserted into tubular element 146; light guides 154 are received in interstice 152 between tube 150 and the outer tubular element 146.

The result is to create a compact module that can be slid onto an inner tube 142 which contains exclusively optical elements, in particular electronic elements.

Figure 11:
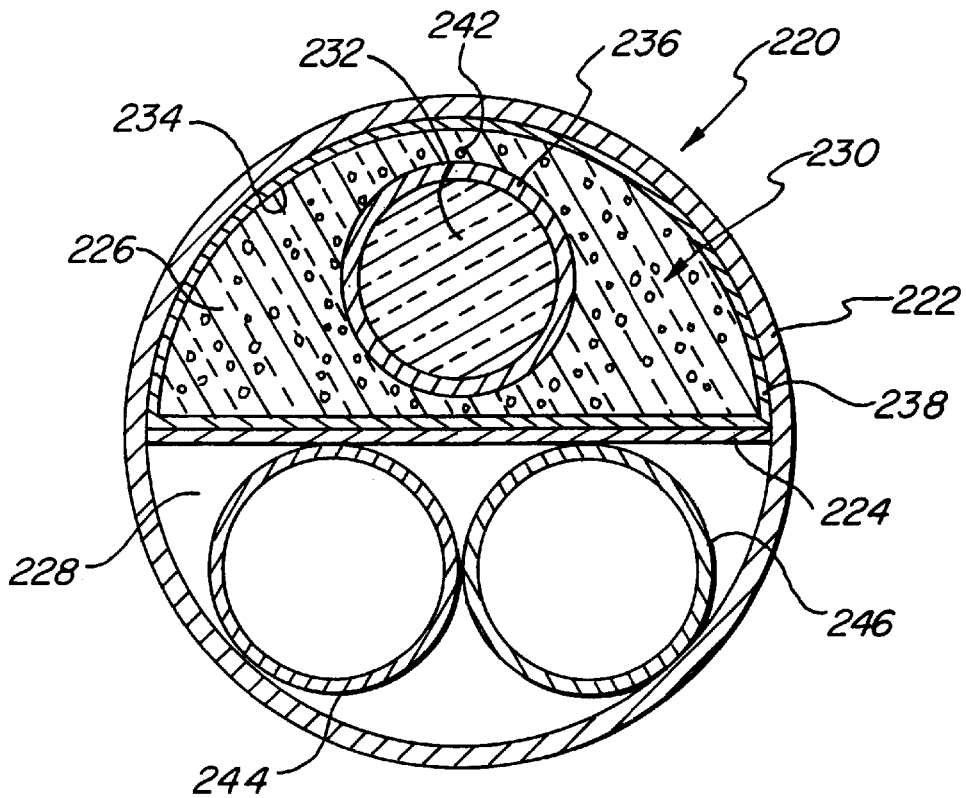
FIG. 11 shows a cross section of a distal end of a further exemplary embodiment of an endoscope, through the closure element.
Figure 12:
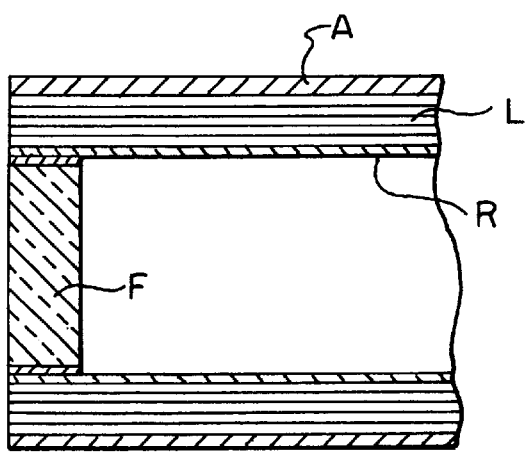
FIG. 12 shows a view, comparable to the representation of FIG. 2, of an endoscope according to the existing art.

FIG. 11 shows a cross section of a distal end of a further exemplary embodiment of an endoscope 220 that has an outer tube 222 that is divided centeredly, by a partition 224, into two regions 226 and 228 separated from one another. Region 226 is closed off at the distal end in hermetically sealed fashion by a closure element 230.

Closure element 230, which has the shape of a semicircular surface, contains at the center a disk 232 that comes to rest in front of a distal end of a distal end (not shown or visible here) of an inner tube that is arranged in region 226. An opaque layer 236 surrounds disk 232.

Disk 232 is received in hermetically sealing fashion in an element 234 which surrounds it and which together with disk 232 forms closure element 230. Element 234 is joined in hermetically sealing fashion, via a layer 238, to the inner side of outer tube 222 and to the side of partition 224 facing toward region 226.

Light guides 242 in the form of glass fibers, which end directly at closure element 230, are arranged in region 226 around the inner tube (not shown here).

Arranged in region 228 are guide tubes 244, 246 which are open toward the outside and through which, for example, instruments or gaseous or liquid media can be passed.

In the sectioned representation of FIG. 11, disk 232 is arranged approximately centeredly in element 234; it can also be arranged at the upper or the lower end depending on the profile of the inner tube.

What is claimed; is:

1. An endoscope comprising
   an outer tube,
   an inner tube disposed within said outer tube,
   optical elements disposed within said inner tube,
   light guides disposed in an interstice between said inner tube and said outer tube, said light guides are guided axially within said interstice toward a distal end of said interstice, and
   a closure element made of a light transparent material for closing off a distal end of said outer tube in hermetically sealed fashion at least in an area of said inner tube and said interstice, said closure element having an outer circumferential surface connected to an inner surface of said distal end of said outer tube, said closure element is provided with a window in an area of a distal end of said inner tube, through which window light can enter into said inner tube, and wherein said window is surrounded circumferentially by an opaque layer which shields said window radially from an entry of light guided via said light guides to said closure element in said interstice, said window is surrounded by said closure element, and wherein said inner tube has a distal end disposed adjacent to an inner side of said window.

2. The endoscope of claim 1, wherein said opaque layer is configured in such a way that it provides not only shielding but also a hermetically sealed join between said window and said closure element surrounding it.

3. The endoscope of claim 1, wherein said opaque layer is made of a material which has a coefficient of thermal expansion that lies in a range of coefficients of thermal expansion of a material of said window and of a material of said closure element surrounding it.

4. The endoscope of claim 1, wherein said opaque layer is applied onto a circumferential outer surface of said window.

5. The endoscope of claim 1, wherein said opaque layer is provided on a radially inner circumferential surface of said closure element surrounding said window.

6. The endoscope of claim 1, wherein said opaque layer is made of a metallic material.

7. The endoscope of claim 6, wherein said metallic material is applied by a measure selected from the group consisting of fusing a pre-fabricated coating layer, sintering, chemical (CVD) vapor deposition, physical (PVD) vapor deposition.

8. The endoscope of claim 1, wherein said outer circumferential surface of said closure element is coated with a material that creates a hermetically sealed join with said inner surface of said outer tube.

9. The endoscope of claim 8, wherein a material having a same composition as provided for joining said window and said closure element surrounding it together.

10. The endoscope of claim 1 wherein said opaque layer is configured as a light-reflecting layer.

11. The endoscope of claim 1, wherein a distally outer surface of said closure element is equipped with a light-reflecting layer, said distally outer surface surrounding said window.

12. The endoscope of claim 1, wherein said opaque layer, and a layer provided on said outer circumferential surface of said closure element for joining said closure element to said inner surface of said outer tube are both made of solderable material.

13. The endoscope of claim 1, wherein said closure element is configured as a ring, in which said window sits in a centeredly fitted fashion.

14. The endoscope of claim 1, wherein when viewing directions for viewing through said endoscope are angled, said closure element is arranged obliquely with respect to a longitudinal center axis of said outer tube.

15. The endoscope of claim 1, wherein said outer tube is configured as a tubular element which can be pulled off from said endoscope and is slidable over a shaft tube bearing said inner tube, said closure element closes off said pull-off tubular element at its distal end in hermetically sealed fashion.

16. The endoscope of claim 15, wherein said light guides are installed in said pull-off tubular element.

17. The endoscope of claim 16, wherein said tubular pull-off element is configured as a rigid tube.

18. The endoscope of claim 16, wherein said tubular element is configured as a flexurally limp hose.

19. The endoscope of claim 18, wherein said closure element is provided with a support, against which support a distal end of said shaft tube comes into contact in a defined position.

20. The endoscope of claim 1, wherein a light connector is provided in a proximal region of said endoscope, said light guides are guided up to said light connector, said light connector is closed off in a hermetically sealed fashion by a light connector window.

21. The endoscope of claim 20, wherein said light connector window of said light connector is coated with a material that creates a hermetically sealed joint with an inner surface of said light connector.

22. The endoscope of claim 1, wherein said closure element is configured, in a region through which illumination light is passed, as an optically effective element.

23. The endoscope of claim 22, wherein said optically effective element is designed with a measure selected from the group of a diffuser and a focusing lens.

24. The endoscope of claim 1, wherein said closure element is shaped, in a region through which an illumination light guided via said light guide is passed in such a way that a deflection of said illumination light out of a guide axis is accomplished.

25. The endoscope of claim 24, wherein said shaping is such that flattened areas are present on at least one of an outer side and an inner side of said closure element.

26. The endoscope of claim 1, wherein said window is configured as an optically effective element.

27. The endoscope of claim 1, wherein said closure element is configured so as to absorb IR light.

28. The endoscope of claim 27, wherein said opaque layer which surrounds said window is transparent to IR light.

29. The endoscope of claim 1, wherein at least one of an inner side of said window and an outer side of said closure element is coated with a layer that reflects IR light.

30. The endoscope of claim 1, wherein an inner side of said closure element is coated, in a region in which said light guides terminate, with a semi-permeable layer that is transparent in an illumination direction and blocks light in opposite direction.

31. A method for manufacturing a closure element for closing off a distal end of an endoscope as defined in claim 1, characterized by the steps of a) preparing a long, rod-shaped, transparent material having a cross section of said window;

b) preparing a long, tubular, transparent material having an inner cavity into which inner cavity said long rod-shaped material from step a) can be introduced so as to fit approximately;

c) providing an opaque layer between an outer side of the rod-shaped material and an inner side of said cavity;

d) sliding said rod-shaped material and said tubular material into one another;

e) joining said outer side of said rod-shaped material in permanent and sealed fashion to the inner side of said cavity; and f) cutting said rod-shaped material and tubular material assembled in step e) into individual disk-shaped closure elements.

32. The method of claim 31, wherein in step c) said outer side of said rod-shaped material is equipped with said opaque layer.

* * * * *